(12) United States Patent
Kraft

(10) Patent No.: US 7,393,822 B2
(45) Date of Patent: Jul. 1, 2008

(54) ESTERS AND THEIR USE IN PERFUMERY

(75) Inventor: Philip Kraft, Dübendorf (CH)

(73) Assignee: Givaudan SA, Vernir (CH)

( * ) Notice: Subject to any disclaimer, the term of this patent is extended or adjusted under 35 U.S.C. 154(b) by 610 days.

(21) Appl. No.: 10/534,426

(22) PCT Filed: Nov. 24, 2003

(86) PCT No.: PCT/CH03/00772

§ 371 (c)(1),
(2), (4) Date: May 10, 2005

(87) PCT Pub. No.: WO2004/050602

PCT Pub. Date: Jun. 17, 2004

(65) Prior Publication Data

US 2006/0046955 A1    Mar. 2, 2006

(30) Foreign Application Priority Data

Nov. 29, 2002  (GB)  ................. 0227807.5

(51) Int. Cl.
*A61Q 13/00* (2006.01)
*A61K 8/18* (2006.01)
*C11D 3/50* (2006.01)

(52) U.S. Cl. ............... 512/8; 512/25; 512/26; 512/27; 510/102; 510/105; 510/106; 510/107

(58) Field of Classification Search .......... 512/8, 512/25, 26, 27; 510/102, 105, 106, 107
See application file for complete search history.

(56) References Cited

U.S. PATENT DOCUMENTS 5,166,412 A    11/1992    Giersch et al. ............ 560/231

FOREIGN PATENT DOCUMENTS

| EP | 472966 | 3/1992 |
|---|---|---|
| EP | 1 262 474 A | 12/2002 |
| WO | WO 00/14051 | * 3/2000 |

OTHER PUBLICATIONS

International Search Report dated Mar. 2, 2004 for Application PCT/CH03/00772.
Search Report dated Apr. 15, 2003 from The Patent Office in Great Britain for Application GB 0227807.5.

* cited by examiner

*Primary Examiner*—Brian P Mruk
(74) *Attorney, Agent, or Firm*—Norris McLaughlin & Marcus, PA

(57) ABSTRACT

This invention relates to unsaturated alicyclic carbonyl compounds of formula (I)

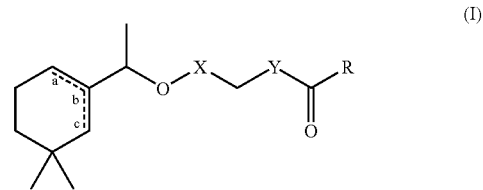

wherein
R is $C_1$ to $C_4$ alkyl; or
R is vinyl or a linear, branched or cyclic $C_3$ to $C_4$ alkenyl;
X is carbonyl or a divalent radical —$(CMe_2)$—; and
Y is oxygen or a divalent radical —$(CH_2)$—.

8 Claims, No Drawings

ESTERS AND THEIR USE IN PERFUMERY

This invention relates to new odourant compounds having musk characteristics, their manufacture and their use in fragrance compositions.

Conventional compounds having musk characteristics have been selected from nitro arenes, polycyclic aromatics and macrocyclic compounds. However, in recent years there has been great activity to find novel compounds having musk characteristics to replace these conventional musks, the use of which is becoming more restricted because of, e.g. environmental concerns.

In recent years, research activity has resulted in the development of new classes of compounds with musk characteristics. EP 472966, for example describes a family of compounds exemplified by the product Helvetolide (1) that is described as having musky, ambrette-like characteristics. Further attempts were made to improve on the olfactory properties of Helvetolide (1) and its related compounds by replacing the gem-dialkyl group in the aliphatic side chain by a carbonyl group, as disclosed in WO 00/14051, exemplified by compound (2) that has been described as having a stronger musky smell than prior art compounds.

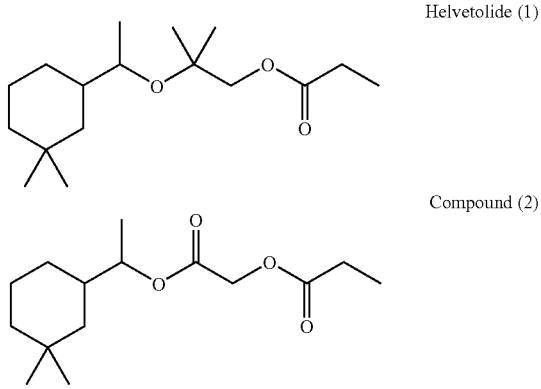

Helvetolide (1)

Compound (2)

Surprisingly, we now found certain unsaturated alicyclic carbonyl compounds that have musk characteristics and a high impact in perfume formulations.

Thus, the present invention refers in a first aspect to a compound of formula (I)

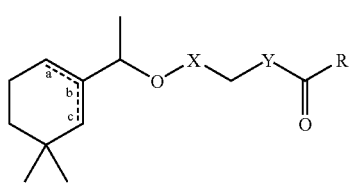

(I)

wherein

R is $C_1$ to $C_4$ alkyl, for example methyl, ethyl, i-propyl, n-propyl, n-butyl, sec-butyl, tert-butyl, cyclopropyl, cyclobutyl; or R is vinyl or a linear, branched or cyclic $C_3$ to $C_4$ alkenyl, for example propen-1-yl, propen-2-yl, or prop-2-en-1-yl, butenyl, e.g. but-1-en-1-yl, cyclobut-1-en-1-yl, or butadienyl, e.g. buta-2,4-dien-1-yl;

X is carbonyl or a divalent radical —($CMe_2$)—;
Y is oxygen or a divalent radical —($CH_2$)—;
the bond between C-a and C-b is a single bond and the bond between C-b and C-c together with the dotted line represents a double bond; or
the bond between C-a and C-b together with the dotted line represents a double bond and the bond between C-b and C-c is a single bond.

The compounds according to the present invention may comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Preferred compounds of formula (I) are propanoic acid 2'-[1''-(3''',3'''-dimethylcyclohex-1'''-enyl)ethoxy]-2'-methylpropyl ester, cyclopropanecarboxylic acid 2'-[1''-(3''',3'''-dimethylcyclohex-1'''-enyl)ethoxy]-2'-methylpropyl ester, propionic acid 2'-[1''-(5''',5'''-dimethylcyclohex-1'''-enyl)ethoxy]-2'-methylpropyl ester, cyclopropanecarboxylic acid 2'-[1''-(5''',5'''-dimethylcyclohex-1'''-enyl)ethoxy]-2'-methylpropyl ester, propionic acid 1''-(5''',5'''-dimethylcyclohex-1'''-enyl)ethoxycarbonylmethyl ester, and cyclopropanecarboxylic acid 1''-(5''',5'''-dimethylcyclohex-1'''-enyl)ethoxycarbonylmethyl ester.

Particular preferred are compounds of formula (I) wherein the bond between C-b and C-c together with the dotted line represents a double bond and the bond between C-a and C-b is a single bond, e.g. propanoic acid 2'-[1''-(3''',3'''-dimethylcyclohex-1'''-enyl)ethoxy]-2'-methylpropyl ester and cyclopropanecarboxylic acid 2'-[1''-(3''',3'''-dimethylcyclohex-1'''-enyl)ethoxy]-2'-methylpropyl ester.

Compounds of formula (I) having a double bond between C-b and C-c are more powerful and possess more distinct musk notes, while compounds having a double bond between C-a and C-b possess more pronounced fruity, green aspects besides their main musk character.

The compounds according to the present invention may be used alone or in combination with known odourant molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example carrier materials, and other auxiliary agents commonly used in the art.

The following list comprises examples of known odourant molecules, which may be combined with the compounds of the present invention:

ethereal oils and extracts, e.g. castoreum, costus root oil, oak moss absolute, geranium oil, jasmin absolute, patchouli oil, rose oil, sandalwood oil or ylang-ylang oil;

alkohols, e.g. citronellol, Ebanol™, eugenol, geraniol, Super Muguet™, linalool, phenylethyl alcohol, Sandalore™, terpineol or Timberol™.

aldehydes and ketones, e.g. α-amylcinnamaldehyd, Georgywood™, hydroxycitronellal, Iso E Super™, Isoraldeine, Hedione™, maltol, methyl cedryl ketone, methylionone or vanillin;

ether and acetals, e.g. Ambrox™, geranyl methyl ether, rose oxide or Spirambrene™ esters and lactones, e.g. benzyl acetat, cedryl actetate, γ-decalactone, Helvetolide® (1), γ-undecalactone or vetiveryl acetate.

macrocycles, e.g. ambrettolide, ethylene brassylate or Exaltolide®.

heterocycles, e.g. isobutylchinoline.

However, due to their unique character, the compounds of formula (I) are especially well suited for use in fresh musky accords, woody-spicy or floral-hesperidic compositions as is more specifically illustrated in the Example.

The compounds of the present invention may be used in a broad range of fragrance applications, e.g. in any field of fine and functional perfumery, such as perfumes, household products, laundry products, body care products and cosmetics. The compounds can be employed in wide ranging amounts depending upon the specific application and on the nature and quantity of other odourant ingredients, that may be for example, from about 0.001 to about 20 weight percent. In one embodiment compounds of the present invention may be employed in a fabric softener in an amount of about 0.001 to 0.05 weight percent.

In another embodiment compounds of the present invention may be used in an alcoholic solution in amounts of about 0.1 to 20 weight percent, more preferably between about 0.1 and 5 weight percent. However, these values should not be limiting on the present invention, since the experienced perfumer may also achieve effects or may create novel accords with lower or higher concentrations.

The compounds of the present invention may be employed into the fragrance application simply by direct mixing the fragrance composition with the fragrance application, or they may, in an earlier step be entrapped with an entrapment material such as for example polymers, capsules, microcapsules and nanocapsules, liposomes, film formers, absorbents such as for example by using carbon or zeolites, cyclic oligosaccharides and mixtures thereof, or they may be chemically bound to substrates which are adapted to release the fragrance molecule upon application of an exogenous stimulus such as light, enzyme, or the like, and then mixed with the application.

Compounds of formula (I) may be prepared starting from a corresponding allylic alcohol, which is accessible either by reduction of Artemone (1-(3',3'-dimethylcyclohex-1'-enyl) ethanone; trademark of Givaudan SA, Switzerland), or by Rupe rearrangment of 1-ethynyl-3,3-dimethylcyclohexanol.

By etherification of the corresponding allylic alcohol with isobutylene oxide and subsequent esterification with the corresponding carboxylic acids compounds of formula (I) wherein X is a divalent radical —$(CMe_2)$-, and Y is oxygen, i.e. oxa esters, may be synthesized.

Compounds of formula (I) wherein X is carbonyl and Y oxygen, i.e. diester, may be synthesized by esterification of the corresponding allylic alcohol with chloroacetic acid, followed by further esterification with the corresponding carboxylic acids.

Compounds of formula (I) wherein X is carbonyl and Y is a divalent radical —$(CH_2)$—, i.e. oxo ester, may be prepared by esterification of the corresponding allylic alcohol with the corresponding oxo carboxylic acids, e.g. laevulinic acid.

Compounds of formula (I) wherein X is a divalent radical —$(CMe_2)$- and Y is a divalent radical —$(CH_2)$—, i.e. oxa ketones may be prepared by etherification of the corresponding allylic alcohol with isobutylene oxide, subsequent oxidation to the aldehyde followed by a Wittig-Horner-Emmons reaction well known in the art and selective hydrogenation of the formed double bond.

Further particulars as to reaction conditions are provided in the examples.

There now follows a series of examples that illustrate the invention.

EXAMPLE 1

Propanoic acid 2'-[1''-(3''',3'''-dimethylcyclohex-1'''-enyl)ethoxy]-2'-methyl-propyl ester A solution of Artemone [1-(3',3'-dimethylcyclohex-1'-enyl)ethanone, commercial product of Givaudan, 152 g, 1.00 mol] in $Et_2O$ (500 ml) was added dropwise with stirring within 3 h at room temp. to a suspension of lithium aluminum hydride (LAH, 10.4 g, 275 mmol) in $Et_2O$ (1 L). The reaction mixture was heated to reflux for 150 min., and after cooling down to 0° C. quenched by careful dropwise addition of water (50 ml). Then 2N aq. HCl (200 ml) was added, and the mixture was poured into water (200 ml). The product was extracted with $Et_2O$ (2×500 ml), and the combined extracts were washed with water (200 ml) and brine (100 ml), dried ($Na_2SO_4$) and evaporated to dryness. The resulting residue (154 g) was purified by silica-gel FC (pentane/$Et_2O$, 4:1) to afford 133 g (87%) of 1-(3',3'-dimethylcyclohex-1'-enyl) ethanol.

During a period of 1 h, a 1 M solution of $MeAlCl_2$ (150 ml, 150 mmol) in hexane was added dropwise with stirring at 0° C. to a solution of 1-(3',3'-dimethylcyclohex-1'-enyl)ethanol (46.3 g, 300 mmol) and isobutylene oxide (26.0 g, 360 mmol) in cyclohexane (300 ml). The cooling bath was removed, and stirring was continued at room temp. for 20 h, prior to pouring the reaction mixture into ice/water (1:1, 200 ml). Conc. aq. $H_3PO_4$ was added until the slurry dissolved, and the product was extracted with $Et_2O$ (2×200 ml). The combined organic extracts were washed with water (200 ml) and brine (25 ml), dried ($Na_2SO_4$) and concentrated in a rotary evaporator. The resulting residue (60.5 g) was purified by silica-gel FC (pentane/$Et_2O$, 9:1, $R_f$=0.14) followed by distillation at 55° C./1.5 mbar to furnish 12.7 (19%) of 2-[1'-(3'',3''-dimethylcyclohex-1''-enyl)ethoxy]-2-methylpropan-1-ol.

At 0° C. under $N_2$, N,N'-Dicyclohexylcarbodiimide (DCC, 2.27 g, 11.0 mmol) was added to a stirred solution of 2-[1'-(3'',3''-dimethylcyclohex-1''-enyl)ethoxy]-2-methylpropan-1-ol (2.26 g, 10.0 mmol), propionic acid (740 mg, 10.0 mmol) and 4-(dimethyl amino)pyridine (DMAP, 120 mg, 1.00 mmol) in $CH_2Cl_2$ (15 ml). The cooling bath was removed and the reaction mixture was stirred for 2 h at room temp. prior to vacuum filtration of the precipitate. The precipitate was washed with $CH_2Cl_2$ (2×), and the combined filtrates were concentrated under reduced pressure. The crude material (3.25 g) was purified by silica-gel FC (pentane/$Et_2O$, 19:1, $R_f$=0.46) to afford 2.52 g (89%) of the odoriferous title compound.

IR (ATR): $v$=1741 $cm^{-1}$ (s, vO=CO), 1168/1068 $cm^{-1}$ (s, vC—O), 1366 $cm^{-1}$ (m, $\delta CH_3$).—$^1$H NMR ($CDCl_3$): δ=0.93/0.94 (2s, 6H, 3'''-$Me_2$), 1.14 (d, J=6.5 Hz, 3H, 2''-$H_3$), 1.16 (t, J=7.5 Hz, 3H, 3-$H_3$), 1.17/1.18 (2s, 6H, 2'-$Me_2$), 1.37 ($m_c$, 2H, 4'''-$H_2$), 1.60 ($m_c$, 2H, 5'''-$H_2$), 1.81-2.06 (m, 2H, 6'''-$H_2$), 2.37 (q, J=7.5 Hz, 2H, 2-$H_2$), 3.90 (d, J=11.0 Hz, 1H, 1'-$H_b$), 3.99 (q, J=7.5 Hz, 1H, 1''-H), 4.01 (d, J=11.0 Hz, 1H, 1'-$H_a$), 5.30 (s, 1H, 2'''-H).—$^{13}$C NMR ($CDCl_3$): δ=8.99 (q, C-3), 19.6 (t, C-5'''), 22.4 (q, C-2''), 23.4 (t, C-6'''), 23.5/23.6 (2q, 2'-$Me_2$), 27.5 (t,C-2), 29.3/29.9 (2q, 3'''-$Me_2$), 31.2 (s, C-3'''), 37.3 (t, C-4'''), 69.7 (t, C-1'), 72.2 (d, C-1''), 74.3 (s, C-2'), 131.3 (d, C-2'''), 139.0 (s, C-1'''), 174.1 (s, C-1).—MS (70 eV); m/z=153 (15) $[C_{10}H_{17}O^+]$, 147 (3) $[C_7H_{15}O_3^+]$, 137

(67) $[C_{10}H_{17}^+]$, 129 (36) $[C_7H_{13}O_2^+]$, 121 (29) $[C_9H_{13}^+]$, 107 (17) $[C_8H_{11}^+]$, 95 (28) $[C_7H_{11}^+]$, 93 (27) $[C_7H_9^+]$, 79 (19) $[C_6H_7^+]$, 57 (100) $[C_3H_5^+]$.

Odor description: Musky, powerful, powdery, slightly animalic.

EXAMPLE 2

Cyclopropanecarboxylic acid 2'-[1"-(3''',3'''-dimethylcyclohex-1'''-enyl)-ethoxy]-2'-methylpropyl ester Following the same procedure according to Example 1, Steglich esterification of 2-[1'-(3",3"-dimethylcyclohex-1"-enyl)ethoxy]-2-methylpropan-1-ol (2.26 g, 10.0 mmol) with cyclopropanecarboxylic acid (860 mg, 10.0 mmol), and purification by silica-gel FC (pentane/Et$_2$O, 19:1, R$_f$=0.33) furnished 2.68 (91%) of cyclopropanecarboxylic acid 2'-[1"-(3''',3'''-dimethylcyclohex-1'''-enyl)ethoxy]-2'-methylpropyl ester.

IR (ATR): ν=1731 cm$^{-1}$ (s, νO═CO), 1153/1068 cm$^{-1}$ (s, νC—O), 1400/1381/1366 cm$^{-1}$ (m, δCH$_3$).—$^1$H NMR (CDCl$_3$): δ=0.87 (m$_c$, 2H, 3-,4-H$_b$), 0.93/0.94 (2s, 6H, 3'''-Me$_2$), 1.02 (m$_c$, 2H, 3-,4-H$_a$), 1.15 (d, J=6.5 Hz, 3H, 2"-H$_3$), 1.17/1.18 (2s, 6H, 2'-Me$_2$), 1.38 (m$_c$, 2H, 4'''-H$_2$), 1.62 (m$_c$, 2H, 5'''-H$_2$), 1.81-2.06 (m, 2H, 6'''-H$_2$), 3.89 (d, J=11.0 Hz, 1H, 1'-H$_b$), 3.98 (q, J=7.5 Hz, 1H, 1"-H), 4.00 (d, J=11.0 Hz, 1H, 1'-H$_a$), 5.30 (s, 1H, 2'''-H).—$^{13}$C NMR (CDCl$_3$): δ=8.18/8.19 (2t, C-3,-4), 12.8 (d, C-2), 19.6 (t, C-5'''), 22.4 (q, C-2"), 23.4 (t, C-6'''), 23.5 (2q, 2'-Me$_2$), 29.3/29.9 (2q, 3'''-Me$_2$), 31.2 (s, C-3'''), 37.3 (t, C-4'''), 69.8 (t, C-1'), 72.2 (d, C-1"), 74.3 (s, C-2'), 131.3 (d, C-2'''), 139.0 (s, C-1'''), 174.5 (s, C-1).—MS (70 eV); m/z=294 (1) [M$^+$], 279 (1) [M$^+$-CH$_3$], 159 (3) $[C_8H_{15}O_3^+]$, 153 (22) $[C_{10}H_{17}O^+]$, 141 (30) $[C_8H_{13}O_2^+]$, 137 (61) $[C_{10}H_{17}^+]$, 121 (27) $[C_9H_{13}^+]$, 107 (17) $[C_8H_{11}^+]$, 95 (26) $[C_7H_{11}^+]$, 93 (25) $[C_7H_9^+]$, 81 (27) $[C_6H_9^+]$, 79 (17) $[C_6H_7^+]$, 69 (100) $[C_5H_9^+]$.

Odor description Musky, pleasant, powdery, strong.

EXAMPLE 3

Propionic acid 2'-[1"-(5''',5'''-dimethylcyclohex-1'''-enyl)ethoxy]-2'-methyl-propyl ester Phosphorus pentoxide (33.1 g, 233 mmol) was added to a solution of 1-ethynyl-3,3-dimethylcyclohexanol (152 g, 1.00 mol) in MePh (800 ml). The slurry was heated to reflux, and stirred at this temp. for 90 min. The reaction mixture was allowed to cool to room temp., and then poured into ice/water (1:1, 500 ml). The product was extracted with Et$_2$O (2×500 ml), and the combined organic extracts were washed with water (500 ml) and brine (100 ml), dried (Na$_2$SO$_4$) and concentrated under reduced pressure. Silica-gel FC (pentane/Et$_2$O, 9:1, R$_f$=0.70) provided 13.8 g (9%) of 1-(5',5'-dimethylcyclohex-1'-enyl)ethanone.

A solution of 1-(5',5'-dimethylcyclohex-1'-enyl)ethanone (13.1 g, 85.8 mmol) in Et$_2$O (50 ml) was added dropwise with stirring within 50 min. to a suspension of LAH (895 mg, 23.6 mmol) in Et$_2$O (150 ml). The reaction mixture was refluxed for 1 h prior to quenching at 0° C. by careful addition of water (50 ml) followed by 5 N aq. HCl (50 ml). The organic layer was separated and the aqueous one extracted with Et$_2$O. The combined ethereal solutions were washed with water and brine, dried (Na$_2$SO$_4$), and concentrated in a rotary evaporator. Silica-gel FC (pentane/Et$_2$O, 9:1, R$_f$=0.14) of the resulting residue (14.7 g) gave 11.2 g (85%) of 1-(5',5'-dimethylcyclohex-1'-enyl)ethanol.

At 0° C. under N$_2$, a 1 M solution of MeAlCl$_2$ (33.6 ml, 33.6 mmol) in hexane was added dropwise during 1 h to a stirred solution of 1-(5',5'-dimethyl-cyclohex-1'-enyl)ethanol (10.4 g, 67.2 mmol) and isobutylene oxide (5.82 g, 80.7 mmol) in cyclohexane (67 ml). The cooling bath was removed, the reaction mixture stirred at room temp. for 23 h, and then poured into ice/water (1:1, 200 ml). The slurry was brought into solution by addition of conc. aq. H$_3$PO$_4$, and the product was extracted with Et$_2$O (2×100 ml). The combined organic extracts were washed with water (100 ml) and brine (25 ml), dried (Na$_2$SO$_4$), and concentrated in a rotary evaporator. The crude material (12.4 g) was purified by silica-gel FC (pentane/Et$_2$O, 9:1, R$_f$=0.17) to provide 3.31 g (22%) of 2-[1'-(5",5"-dimethylcyclohex-1"-enyl)ethoxy]-2-methyl-propan-1-ol.

Following the same procedure according to Example 1, Steglich esterification of 2-[1'-(5",5"-dimethylcyclohex-1"-enyl)ethoxy]-2-methylpropan-1-ol (1.29 g, 5.70 mmol) with propionic acid (420 mg, 5.70 mmol), and purification by silica-gel FC (pentane/Et$_2$O, 9:1, R$_f$=0.56) furnished 420 mg (26%) of propionic acid 2'-[1"-(5''',5'''-dimethylcyclohex-1'''-enyl)ethoxy]-2'-methylpropyl ester.

IR (ATR): ν=1169/1068 cm$^{-1}$ (s, νC—O), 1741 cm$^{-1}$ (s, νO═CO), 1365 cm$^{-1}$ (m, δCH$_3$).—$^1$H NMR (CDCl$_3$): δ=0.89/0.91 (2s, 6H, 5'''-Me$_2$), 1.14 (d, J=6.5 Hz, 3H, 2"-H$_3$), 1.16 (t, J=7.5 Hz, 3H, 3-H$_3$), 1.17/1.18 (2s, 6H, 2'-Me$_2$), 1.29 (t, J=6.5 Hz, 2H, 4'''-H$_2$), 1.69 (dd, J=17.0, 2.0 Hz, 1H, 6'''-H$_b$), 1.83 (dd, J=17.0, 2.0 Hz, 1H, 6'''-H$_a$), 2.01 (m$_c$, 2H, 3'''-H$_2$), 2.36 (q, J=7.5 Hz, 2H, 2-H$_2$), 3.92 (d, J=11.0 Hz, 1H, 1'-H$_b$), 4.00 (d, J=11.0 Hz, 1H, 1'-H$_a$), 4.02 (q, J=6.5 Hz, 1H, 1"-H), 5.54 (s, 1H, 2'''-H).—$^{13}$C NMR (CDCl$_3$): δ=8.98 (q, C-3), 22.4 (q, C-2"), 22.7 (t, C-3'''), 23.4 (t, C-6'''), 23.4/23.6 (2q, 2'-Me$_2$), 27.5 (t,C-2), 27.9/28.0 (2q, 5'''-Me$_2$), 28.6 (s, C-5'''), 35.2 (t, C-4'''), 37.5 (t, C-6'''), 69.8 (t, C-1'), 71.9 (d, C-1"), 74.2 (s, C-2'), 119.1 (d, C-2'''), 140.4 (s, C-1'''), 174.1 (s, C-1).—MS (70 eV); m/z=153 (16) $[C_{10}H_{17}O^+]$, 147 (2) $[C_7H_{15}O_3^+]$, 137 (59) $[C_{10}H_{17}^+]$, 129 (30) $[C_7H_{13}O_2^+]$, 121 (37) $[C_9H_{13}^+]$, 107 (29) $[C_8H_{11}^+]$, 95 (29) $[C_7H_{11}^+]$, 93 (39) $[C_7H_9^+]$, 79 (48) $[C_6H_7^+]$, 57 (100) $[C_4H_9^+]$.

Odor description: Musky, powdery, fruity.

EXAMPLE 4

Cyclopropanecarboxylic acid 2'-[1"-(5''',5'''-dimethylcyclohex-1'''-enyl)-ethoxy]-2'-methylpropyl ester Following the same procedure according to Example 1, Steglich esterification of 2-[1'-(5",5"-dimethylcyclohex-1"-enyl)ethoxy]-2-methylpropan-1-ol (1.29 g, 5.70 mmol) with cyclopropanecarboxylic acid (490 mg, 5.70 mmol), and purification by silica-gel FC (pentane/Et$_2$O, 9:1, R$_f$=0.58) furnished 590 mg (35%) of cyclopropanecarboxylic acid 2'-[1"-(5''',5'''-dimethylcyclohex-1'''-enyl)ethoxy]-2'-methylpropyl ester.

IR (ATR): ν=1163/1067 cm$^{-1}$ (s, νC—O), 1730 cm$^{-1}$ (s, νO═CO), 1382/1400/1382 cm$^{-1}$ (m, δCH$_3$).—$^1$H NMR (CDCl$_3$): δ=0.85 (dt, J=8.0, 4.5 Hz, 2H, 3-,4-H$_b$), 0.89/0.91 (s, 6H, 5'''-Me$_2$), 1.01 (dt, J=8.0, 4.5 Hz, 2H, 3-,4-H$_a$), 1.14 (d, J=6.5 Hz, 3H, 2"-H$_3$), 1.17/1.18 (2s, 6H, 2'-Me$_2$), 1.29 (dd, J=6.5, 2.5 Hz, 1H, 4-H$_b$), 1.30 (dd, J=6.5, 2.5 Hz, 1H, 4-H$_a$), 1.64 (tt, J=8.0, 4.5 Hz, 1H, 2-H), 1.70 (dd, J=17.0, 2.0 Hz, 1H, 6'''-H$_b$), 1.84 (dd, J=17.0, 2.0 Hz, 1H, 6'''-H$_a$), 2.01 (m$_c$, 2H, 3'''-H$_2$), 3.91 (d, J=11.0 Hz, 1H, 1'-H$_b$), 3.98 (d, J=11.0 Hz, 1H 1'-H$_a$), 4.02 (q, J=6.5 Hz, 1H, 1"-H), 5.54 (s, 1H, 2'''-H).—$^{13}$C NMR (CDCl$_3$): δ=8.14 (2t, C-3,-4), 12.8 (d, C-2), 22.4 (q, C-2"), 22.7 (t, C-3'''), 23.5/23.6 (2q, 2'-Me$_2$), 27.9/28.0 (2q, 5'''-Me$_2$), 28.6 (s, C-5'''), 35.2 (t, C-4'''), 37.5 (t,

C-6'''), 69.8 (t, C-1'), 71.9 (d, C-1''), 74.3 (s, C-2'), 119.1 (d, C-2'''), 140.3 (s, C-1'''), 174.5 (s, C-1).—MS (70 eV); m/z=294 (1) [M$^+$], 159 (2) [$C_8H_{15}O_3^+$], 153 (25) [$C_{10}H_{17}O^+$], 141 (27) [$C_8H_{13}O_2^+$], 137 (54) [$C_{10}H_{17}^+$], 121 (27) [$C_9H_{13}^+$], 107 (22) [$C_8H_{11}^+$], 95 (25) [$C_7H_{11}^+$], 93 (26) [$C_7H_9^+$], 81 (19) [$C_6H_9^+$], 79 (30) [$C_6H_7^+$], 69 (100) [$C_5H_9^+$].

Odor description: Musky, fresh, floral, slightly metallic.

EXAMPLE 5

Propionic acid 1''-(5''',5'''-dimethylcyclohex-1'''-enyl) ethoxycarbonylmethyl ester N,N'-Dicyclohexylcarbodiimide (DCC, 2.58 g, 12.5 mmol) was added at 0° C. under $N_2$ to a solution of 1-(5,5-dimethylcyclohex-1-enyl)ethanol, chloroacetic acid (1.07 g, 11.3 mmol) and 4-(dimethylamino)pyridine (DMAP, 140 mg, 1.13 mmol) in $CH_2Cl_2$ (15 ml). The cooling bath was removed and the reaction mixture was stirred for 1 h at room temp., prior to vacuum filtration of the precipitates. The filtrate was concentrated under reduced pressure, the resulting residue purified by silica-gel FC (pentane/$Et_2O$, 19:1, $R_f$=0.65) to furnish 2.17 g (83%) of chloroacetic acid 1'-(5'',5''-dimethylcyclohex-1''-enyl)ethyl ester.

A mixture of chloroacetic acid 1'-(5'',5''-dimethylcyclohex-1''-enyl)ethyl ester (1.00 g, 4.33 mmol), propionic acid (320 mg, 4.33 mmol), $K_2CO_3$ (1.20 g, 8.67 mmol) and NaBr (450 mg, 4.33 mmol) in $Et_2CO$/dioxane (4:1, 10 ml) was refluxed for 1 day prior to pouring into water (50 ml). The product was extracted with $Et_2O$ (2×50 ml), and the combined extracts were washed with water (50 ml) and brine (25 ml). After drying with $Na_2SO_4$ and evaporation of the solvent under reduced pressure, silica-gel FC (pentane/$Et_2O$, 9:1, $R_f$=0.41) afforded 370 mg (32%) of propionic acid 1''-(5''',5'''-dimethylcyclohex-1'''-enyl)ethoxycarbonylmethyl ester.

IR (ATR): ν=1161 cm$^{-1}$ (s, νC—O), 1747 cm$^{-1}$ (s, νO=CO).—$^1$H NMR (CDCl$_3$): δ=0.89/0.91 (2s, 6H, 5'''-Me$_2$), 1.19 (t, J=7.5 Hz, 3H, 3-H, 3-H$_3$), 1.31 (d, J=6.5 Hz, 3H, 2''-H$_3$), 1.34 (m$_c$, 2H, 4'''-H$_2$), 1.69 (d, J=16.5 Hz, 1H, 6'''-H$_b$), 1.78 (d, J=16.5 Hz, 1H, 6'''-H$_a$), 2.05 (m$_c$, 2H, 3'''-H$_2$), 2.45 (q, J=7.5 Hz, 2H, 2-H$_2$), 4.56 (d, J=16.0 Hz, 1H, 2'-H$_b$), 4.61 (d, J=16.0 Hz, 1H, 2'-H$_a$), 5.32 (q, J=6.5 Hz, 1H, 1''-H), 5.67 (s, 1H, 2'''-H).—$^{13}$C NMR (CDCl$_3$): δ=8.81 (q, C-3), 18.5 (q, C-2''), 22.7 (t, C-3'''), 27.0 (t, C-2), 27.5/28.3 (2q, 5'''-Me$_2$), 28.6 (s, C-5'''), 34.7 (t, C-4'''), 37.5 (t, C-6'''), 60.6 (t, C-2'), 75.5 (d, C-1''), 123.1 (d, C-2'''), 135.2 (s, C-1'''), 167.1 (s, C-1'), 173.5 (s, C-1).—MS (70 eV); m/z=154 (3) [$C_{10}H_{18}O^+$], 136 (58) [$C_{10}H_{16}^+$], 121 (86) [$C_9H_{13}^+$], 107 (75) [$C_8H_{11}^+$], 93 (100) [$C_7H_9^+$], 79 (100) [$C_6H_7^+$], 41 (36) [$C_3H_5^+$].

Odor description: Musky, green.

EXAMPLE 6

Cyclopropanecarboxylic acid 1''-(5''',5'''-dimethylcyclohex-1'''-enyl)ethoxy-carbonylmethyl ester A mixture of chloroacetic acid 1'-(5'',5''-dimethylcyclohex-1''-enyl)ethyl ester (1.00 g, 4.33 mmol), cyclopropanecarboxylic acid (370 mg, 4.33 mmol), $K_2CO_3$ (1.20 g, 8.67 mmol) and NaBr (450 mg, 4.33 mmol) in $Et_2CO$/dioxane (4:1, 10 ml) was refluxed for 1 day prior to pouring into water (50 ml). The product was extracted with $Et_2O$ (2×50 ml), and the combined extracts were washed with water (50 ml) and brine (25 ml). After drying with $Na_2SO_4$ and evaporation of the solvent under reduced pressure, silica-gel FC (pentane/$Et_2O$, 9:1, $R_f$=0.30) afforded 870 mg (72%) of cyclopropanecarboxylic acid 1''-(5''',5'''-dimethylcyclohex-1'''-enyl) ethoxycarbonylmethyl ester.

IR (ATR): ν=1156 cm$^{-1}$ (s, νC—O), 1736 cm$^{-1}$ (s, νO=CO).—$^1$H NMR (CDCl$_3$): δ=0.89/0.91 (2s, 6H, 5'''-Me$_2$), 0.93 (m$_c$, 2H, 3-,4-H$_b$), 1.07 (m$_c$, 2H, 3-,4-H$_a$), 1.30 (d, J=6.5 Hz, 3H, 2''-H$_3$), 1.33 (m$_c$, 2H, 4'''-H$_2$), 1.68-1.80 (m, 3H, 2-H, 6'''-H$_2$), 2.05 (m$_c$, 2H, 3'''-H$_2$), 4.56 (d, J=16.0 Hz, 1H, 2'-H$_b$), 4.61 (d, J=16.0 Hz, 1H, 2'-H$_a$), 5.30 (q, J=6.5 Hz, 1H, 1''-H), 5.67 (s, 1H, 2'''-H).—$^{13}$C NMR (CDCl$_3$): δ=8.67/8.65 (t, C-3,-4), 12.4 (d, C.-2), 18.5 (q, C-2''), 22.7 (t, C-3'''), 27.5/28.3 (2q, 5'''-Me$_2$), 28.5 (s, C-5'''), 34.7 (t, C-4'''), 37.5 (t, C-6'''), 60.6 (t, C-2'), 75.5 (d, C-1''), 123.0 (d, C-2'''), 135.2 (s, C-1'''), 167.1 (s, C-1'), 174.0 (s, C-1).—MS (70 eV); m/z=153 (2) [$C_{10}H_{17}O^+$], 136 (61) [$C_{10}H_{16}^+$], 121 (84) [$C_9H_{13}^+$], 107 (71) [$C_8H_{11}^+$], 93 (98) [$C_7H_9^+$], 79 (100) [$C_6H_7^+$], 69 (34) [$C_5H_9^+$].

Odor description: Musky, green, floral.

EXAMPLE 7

Floral-Musky, Powdery Perfume Formulation for Shower Gel

| | compound/ingredient | parts by weight 1/1000 |
|---|---|---|
| 1. | 6-Acetyl-1,1,2,4,4,7-hexamethyltetralin (Fixolide ™) | 68.00 |
| 2. | Ambrettolide | 6.00 |
| 3. | Benzaldehyde | 0.14 |
| 4. | Citronellol, extra quality | 10.00 |
| 5. | Citronellyl acetate | 1.20 |
| 6. | Dipropylene glycol | 135.40 |
| 7. | Elemi oil | 1.20 |
| 8. | 6-Ethyl-3-methyloct-6-en-1-ol (Super Muguet ™) | 2.00 |
| 9. | 4,6,6,7,8,8-Hexamethyl-1,3,4,6,7,8-hexahydrocyclopenta[g]benzopyran (Galaxolide ™) 50 BB | 560.00 |
| 10. | Hexyl salicylate | 8.00 |
| 11. | 3-trans-Isocamphylcyclohexanol (Sandela ™) | 20.0 |
| 12. | Lemon oil abergapt | 10.00 |
| 13. | Linalool, synthetic | 20.00 |
| 14. | Linalyl acetate, synthetic | 10.00 |
| 15. | 12-Methyl-14-tetradec-9-enolide (Nirvanolide ™) | 2.00 |
| 16. | 15-Pentadecanolide (Thibetolide ™) | 4.00 |
| 17. | 15-Pentadec-11-enolide (Habanolide ™) | 40.00 |
| 18. | 1-Phenylethyl acetate (Gardenol ™) | 1.00 |
| 19. | Rose oxide CO | 0.06 |
| 20. | 1-(2,2,6-Trimethylcyclohexyl)hexan-3-ol (Timberol ™) | 0.20 |
| 21. | Vanillin | 0.80 |
| 22. | Propanoic acid 2'-[1''-(3''',3'''-dimethylcyclohex-1'''-enyl)ethoxy]-2'-methylpropyl ester | 100.00 |

The propanoic acid 2'-[1''-(3''',3'''-dimethylcyclohex-1'''-enyl)ethoxy]-2'-methylpropyl ester forms a very powerful and pleasant musk accord together with the polycyclic and macrocyclic musk odorants, to which it adds freshness, fruitiness and a powdery aspect. This accord conveys smoothness, and richness to the fragrance and imparts a caressing, comfortable feeling to the perfumed product. In combination with the elemi and lemon oils it as well enhances fresh and clean aspects of the perfume and makes it ideally suited for application in shower gels.

The invention claimed is:

1. A compound of formula (I)

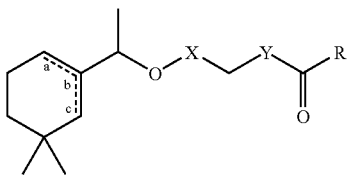

(I)

wherein

R is $C_1$ to $C_4$ alkyl; or

R is vinyl or a linear, branched or cyclic $C_3$ to $C_4$ alkenyl;

X is carbonyl or a divalent radical —($CMe_2$)—;

Y is oxygen or a divalent radical —($CH_2$)—;

the bond between C-b and C-c is a single bond and the bond between C-a and C-b together with the dotted line represents a double bond; or the bond between C-b and C-c together with the dotted line represents a double bond and the bond between C-a and C-b is a single bond.

2. A compound according to claim 1 wherein the bond between C-b and C-c together with the dotted line represents a double bond and the bond between C-a and C-b is a single bond.

3. A compound according to claim 1 wherein the bond between C-b and C-c is a single bond and the bond between C-a and C-b together with the dotted line represents a double bond.

4. A compound according to claim 1 selected from the group consisting of propanoic acid 2'-[1"-(3'",3'"-dimethyl-cyclohex-1'"-enyl)ethoxy]-2'-methylpropyl ester, cyclopropanecarboxylic acid 2'-[1"-(3'",3'"-dimethylcyclohex-1'"-enyl)ethoxy]-2'-methylpropyl ester, propionic acid 2'-[1"-(5'",5'"-dimethylcyclohex-1'"-enyl)ethoxy]-2'-methylpropyl ester, cyclopropanecarboxylic acid 2'-[1"-(5'",5'"-dimethyl-cyclohex-1'"-enyl)ethoxy]-2'-methylpropyl ester, propionic acid 1"-(5'",5'"-dimethylcyclohex-1'"-enyl)ethoxycarbonyl-methyl ester, and cyclopropanecarboxylic acid 1"-(5'",5'"-dimethylcyclohex-1'"-enyl)ethoxycarbonylmethyl ester.

5. A fragrance application comprising a compound according to claim 1.

6. A fragrance application according to claim 5 wherein the fragrance application is a perfume, household product, laundry product, body care product or cosmetic product.

7. A method of imparting a musk odor to a fragrance, comprising the step of:

providing the compound according to claim 1 to the fragrance.

8. A method of imparting a musk odor to a fragrance composition, comprising the step of:

providing the compound according to claim 1 to the fragrance composition.

* * * * *